United States Patent
Ichige

(10) Patent No.: US 10,726,283 B2
(45) Date of Patent: Jul. 28, 2020

(54) FINGER VEIN AUTHENTICATION DEVICE

(71) Applicant: HITACHI, LTD., Tokyo (JP)

(72) Inventor: Kenji Ichige, Tokyo (JP)

(73) Assignee: HITACHI, LTD., Tokyo (JP)

( * ) Notice: Subject to any disclaimer, the term of this patent is extended or adjusted under 35 U.S.C. 154(b) by 43 days.

(21) Appl. No.: 16/060,830

(22) PCT Filed: Oct. 31, 2016

(86) PCT No.: PCT/JP2016/082350
§ 371 (c)(1),
(2) Date: Jun. 8, 2018

(87) PCT Pub. No.: WO2017/098834
PCT Pub. Date: Jun. 15, 2017

(65) Prior Publication Data
US 2018/0336428 A1  Nov. 22, 2018

(30) Foreign Application Priority Data
Dec. 8, 2015  (JP) .................... 2015-239035

(51) Int. Cl.
*G06K 9/00* (2006.01)
*A61B 5/1171* (2016.01)
(Continued)

(52) U.S. Cl.
CPC ........ *G06K 9/00885* (2013.01); *A61B 5/1171* (2016.02); *G01N 21/01* (2013.01);
(Continued)

(58) Field of Classification Search
None
See application file for complete search history.

(56) References Cited

U.S. PATENT DOCUMENTS 5,434,412 A * 7/1995 Sodickson .......... A61B 5/14532
250/343
8,121,354 B2 * 2/2012 Nagasaka ................ G06K 9/00
382/115
(Continued)

FOREIGN PATENT DOCUMENTS

CN  107590425 A * 1/2018
JP  09-106447 A    4/1997
(Continued)

OTHER PUBLICATIONS

Huang et al, Finger-vein Authentication Based on Wide Line Detector and Pattern Normalization, 2010 International Conference on Pattern Recognition (Year: 2010).*

(Continued)

*Primary Examiner* — Andrae S Allison
(74) *Attorney, Agent, or Firm* — Volpe and Koenig, P.C.

(57) ABSTRACT

Provided is a device which performs vein authentication by using a downward irradiation-type thin module and selecting an image of a proper angle by varying the irradiation direction of near-infrared illumination. Realized are a photographing method and control method of a finger vein image suitable for thin devices such as a smartphone. Adopted is a finger vein authentication device comprising an imaging unit, an illumination unit which is disposed on a substantially same plane as the imaging unit, and irradiates a finger to be captured by the imaging unit with light in which an irradiation angle is variable, an image selection unit which selects an image according to the irradiation angle of the illumination unit, and an authentication processing unit which performs authentication processing using the image selected by the image selection unit.

7 Claims, 7 Drawing Sheets

(51) Int. Cl.
*G01N 21/01* (2006.01)
*G06F 21/32* (2013.01)
*G06T 1/00* (2006.01)
*G01N 21/47* (2006.01)

(52) U.S. Cl.
CPC ......... *G06F 21/32* (2013.01); *G06K 9/00013* (2013.01); *G06T 1/0007* (2013.01); *G01N 21/4795* (2013.01); *G06K 2009/0006* (2013.01); *G06K 2009/00932* (2013.01); *G06T 2207/30101* (2013.01)

(56) References Cited

U.S. PATENT DOCUMENTS

| | | | | |
|---|---|---|---|---|
| 8,811,682 | B2* | 8/2014 | Kanda | G06K 9/00046 340/5.83 |
| 2002/0048014 | A1* | 4/2002 | Kono | G06K 9/00 356/71 |
| 2003/0016345 | A1* | 1/2003 | Nagasaka | G06K 9/00013 356/71 |
| 2003/0103686 | A1* | 6/2003 | Ogura | G06K 9/00013 382/321 |
| 2004/0057605 | A1 | 3/2004 | Kono et al. | |
| 2004/0184641 | A1 | 9/2004 | Nagasaka et al. | |
| 2009/0074263 | A1* | 3/2009 | Higuchi | A61B 5/1172 382/126 |
| 2009/0092291 | A1* | 4/2009 | Nagasaka | G07C 9/00158 382/115 |
| 2009/0214083 | A1 | 8/2009 | Sato | |
| 2009/0243798 | A1* | 10/2009 | Fukuda | G06K 9/00375 340/5.82 |
| 2013/0212655 | A1* | 8/2013 | Hoyos | G06K 9/00107 726/5 |
| 2015/0260573 | A1* | 9/2015 | Ishimaru | G01J 3/4532 356/451 |
| 2015/0379708 | A1* | 12/2015 | Abramoff | G06T 7/0012 382/128 |
| 2016/0256079 | A1* | 9/2016 | Shimano | G06K 9/00013 |

FOREIGN PATENT DOCUMENTS

| | | | |
|---|---|---|---|
| JP | 2004-265269 A | | 9/2004 |
| JP | 2006288872 A | * | 10/2006 |
| JP | 2007219625 A | * | 8/2007 |
| JP | 3972779 B2 | | 9/2007 |
| JP | 2008-71137 | * | 3/2008 |
| JP | 2009-165630 A | | 7/2009 |
| JP | 5310908 B2 | * | 8/2012 |

OTHER PUBLICATIONS

Le et al, New Finger Biometric Method Using Near Infrared Imaging, Sensors 2011, 11, 2319-2333; doi:10.3390/s110302319. (Year: 2011).*

International Search Report dated Jan. 24, 2017 for the International Application No. PCT/JP2016/082350.

* cited by examiner (a) UPWARD IRRADIATION (b) LATERAL IRRADIATION (c) DOWNWARD IRRADIATION 1

(d) DOWNWARD IRRADIATION 2

(e) DOWNWARD IRRADIATION 3

FINGER VEIN AUTHENTICATION DEVICE

TECHNICAL FIELD

The present invention relates to a finger vein authentication device.

BACKGROUND ART

Conventionally, known is a finger vein authentication device which registers in advance the vein pattern of a person's finger as biological information, and authenticates or identifies an individual based on the process of matching the foregoing registered biological information and the vein pattern of the presented finger. In PTL 1, a finger vein authentication device includes a light source which irradiates a person's finger with near-infrared light, an imaging unit which captures an image of a vein pattern, and an information processing unit which matches the photographed vein pattern and a pre-stored registered finger vein pattern and determines whether they are a match. In this kind of conventional finger vein authentication device, an optical reduction system is used as the optical system of the imaging unit.

CITATION LIST

Patent Literature

[PTL 1] Japanese Patent No. 3972779

SUMMARY OF THE INVENTION

Problems to be Solved by the Invention

With the devise disclosed in PTL 1, because light from the light source directly illuminates the finger surface to be photographed, it is not possible to obtain sufficient contrast, and it is difficult to extract a clear vein pattern.

Moreover, when attempting to install a finger vein authentication device in a thin digital device such as a smartphone or a tablet, the thickness becomes a problem in the conventional technology.

The present invention was devised in view of the foregoing points, and an object of this invention is to provide a smaller and thinner finger vein authentication device.

Means to Solve the Problems

In order to achieve the foregoing object, adopted is a finger vein authentication device comprising an imaging unit, an illumination unit which is disposed on a substantially same plane as the imaging unit, and irradiates a finger to be captured by the imaging unit with light in which an irradiation angle is variable, an image selection unit which selects an image according to the irradiation angle of the illumination unit, and an authentication processing unit which performs authentication processing using the image selected by the image selection unit.

Advantageous Effects of the Invention

The present invention is able to provide a smaller and thinner finger vein authentication device.

DESCRIPTION OF EMBODIMENTS

The finger vein authentication device according to the embodiments of the present invention is now explained with reference to the appended drawings. The following embodiments are merely exemplifications for explaining the present invention, and the present invention is not limited to these embodiments. Accordingly, the present invention may be implemented in various modes to the extent that such modes do not deviate from the subject matter of the present invention.

Embodiment 1

Figure 1:
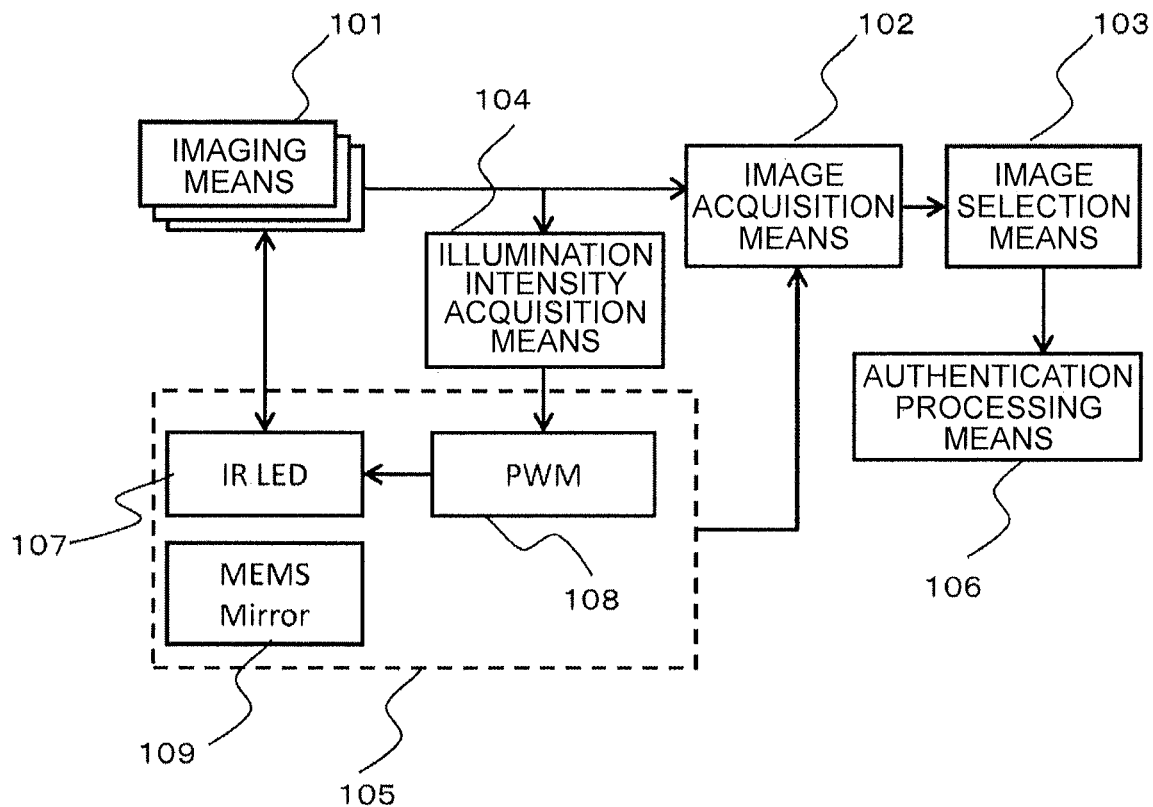
FIG. 1 is a block diagram showing the processing circuit of the finger vein authentication device of the first embodiment.
Figure 2:
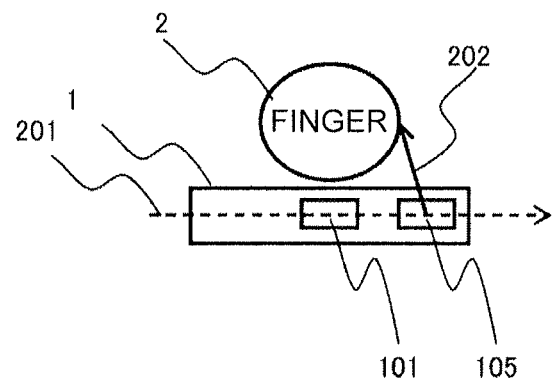
FIG. 2 is a cross section of the finger vein authentication device of the first embodiment.

FIG. 1 is a block diagram showing the processing circuit of the finger vein authentication device according to Embodiment 1, and FIG. 2 is a cross section of the finger vein authentication device including the finger as the object to be authenticated.

As shown in FIG. 1 and FIG. 2, the finger vein authentication device 1 according to Embodiment 1 comprises an imaging means 101 and an illumination means 105, and the imaging means 101 captures a picture of a finger 2 as an object to be authenticated subject to the near-infrared light irradiated by the illumination means 105, and executes, in an authentication processing means 106, image-based authentication processing of the output image data via an image acquisition means 102 and an image selection means 103. The illumination means 105 is configured from a PWM signal generation means 108, a near-infrared light source 107 and a MEMS (Micro Electrical Mechanical Sensor) mirror 109 with an illumination intensity signal output by an illumination intensity acquisition means 104 as the input signal.

The image acquisition means 102 communicates with the illumination means 105, and temporarily retains image data of different irradiation angles in a classifiable state. The retained image data can be read by designating a predetermined irradiation angle.

The image selection means 103 reads the images retained by the image acquisition means 102, and selects an image that is suitable for finger vein authentication based on image processing. As the image selection method to be adopted by the image selection means 103, considered may be a method of preparing a plurality of evaluation functions, calculating the evaluation values of the accuracy of distribution of brightness across the entire image and the contrast (amplitude of light/dark) of the vein image included in the image, performing weighting thereto and calculating a comprehensive evaluation value, and selecting an image with a high evaluation value as the image that is suitable for finger vein authentication.

Due to the optical characteristics of the imaging means 101 and the illumination means 105, all input images contain unevenness of brightness and distortion of image. If correction of the foregoing unevenness of brightness and distortion of image is required as the pre-processing to be performed before the authentication processing, considered may be causing the image selection means 103 to additionally perform image processing of brightness correction or distortion correction to the image selected by the image selection means 103.

The illumination intensity acquisition means 104 determines, with an output signal of the imaging means 101 as the input, the brightness of the finger based on the image data contained therein, and sends a control signal to the PWM signal generation means 108.

The illumination means 105 analyzes the photographed image, and thereby controls the irradiation intensity.

The authentication processing means 106 extracts the feature quantity related to a living individual, a finger vein pattern in this example, based on the output image of the image selection means 103, and matches the finger vein pattern of the individual, which has been retained in advance, with internal registered information. When performing the foregoing matching process, the authentication processing means 106 evaluates the matching level relative to the registered finger vein pattern, and determines that the user is the person himself/herself when the matching level is within a predetermined evaluation range. Here, image-based authentication processing includes pattern registration processing of extracting a vein pattern from an input image as biometric information for identifying the individual and registering the extracted pattern, and pattern matching processing of matching the registered vein pattern and the vein pattern extracted from the input image of the finger that is currently being presented, and determining whether the result coincides with the registered pattern of that individual.

The PWM signal generation means 108 changes the pulse width, and thereby controls the irradiation intensity of light irradiated by the near-infrared light source 107. The MEMS mirror 109 is a mirror in which the direction thereof is changed based on a predetermined frequency and amplitude, and is used for reflecting the near-infrared light irradiated by a near-infrared light source 107 in which the irradiation direction is fixed, and thereby irradiating the respective parts of a finger as the object to be authenticated.

As shown in FIG. 2, the imaging means 101 and the illumination means 105 are disposed on substantially the same plane to make the device thinner. This is so that the finger vein authentication device of the present invention can be installed in a thin device such as a smartphone.

Figure 3:
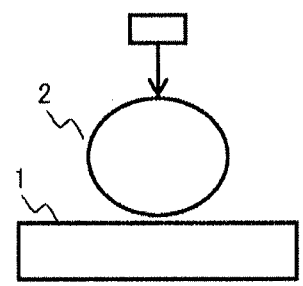
FIG. 3 is a diagram showing the classification of the illumination method of the finger vein authentication device.
Figure 3:
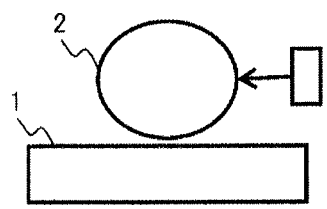
Figure 3:
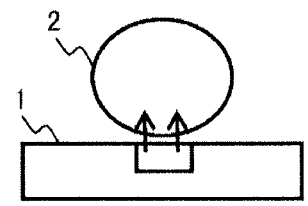
Figure 3:
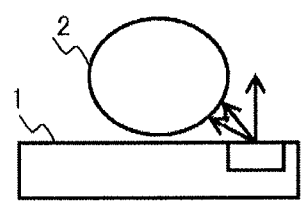
Figure 3:
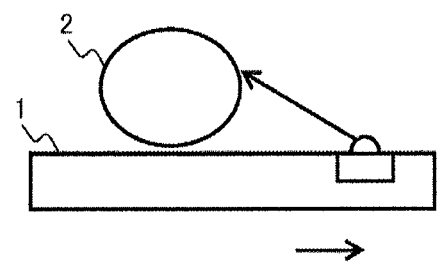

In order to clarify the difference between the illumination means 105 in this embodiment and a conventional illumination means, the classification of a conventional finger vein illumination method is shown in FIG. 3. In FIG. 3(a) and FIG. 3(b), the illumination part is disposed at a position in which the height differs from the finger vein authentication device 1 comprising the imaging means, and is unsuitable for making the device thinner. The illumination method corresponding to the challenge of making the device thinner is the downward irradiation method of FIG. 3(c), FIG. 3(d) and FIG. 3(e), and the device can be thinned by disposing the finger vein authentication device 1 and the illumination part on substantially the same plane as described above.

The method of FIG. 3(c) is a method of placing the illumination part immediately below the finger and taking a photo of the finger vein, but it is difficult to obtain the contrast of the vein pattern upon taking a photo of the finger vein. The method of FIG. 3(d) is a method of placing the light source at a position shifted from immediately below the finger, and irradiating at a broad angle. Here, the installation position of the light source and the broadness of the irradiation angle need to be decided upon giving consideration to fingers of various sizes to be authenticated. It is not possible to obtain a favorable condition for all fingers, and, as a result of setting an average thickness of fingers as the criteria, there are cases where the proper illumination effect cannot be obtained. Moreover, because the finger is irradiated at a broad angle, there are cases where the light does not reach the finger and the energy becomes wasted, which is inefficient. The method of FIG. 3(e) is a method of placing the light source at a position significantly shifted from immediately below the finger, and irradiating at a narrow angle. As a result of irradiating from a position that is farther from immediately below the finger, it is possible to irradiate the top side of the finger even for fingers of different thicknesses, and the contrast of the finger vein image can be increased with more transmitted light components. Nevertheless, if the distance from immediately below the finger is increased, there is a drawback in that the width of the device will also increase.

The illumination means 105 of FIG. 2 performs proper illumination to fingers of various sizes and shapes by disposing the illumination part at a position shifted from immediately below the finger, irradiating the finger at a narrow angle, and adjusting the irradiation angle.

Figure 4:
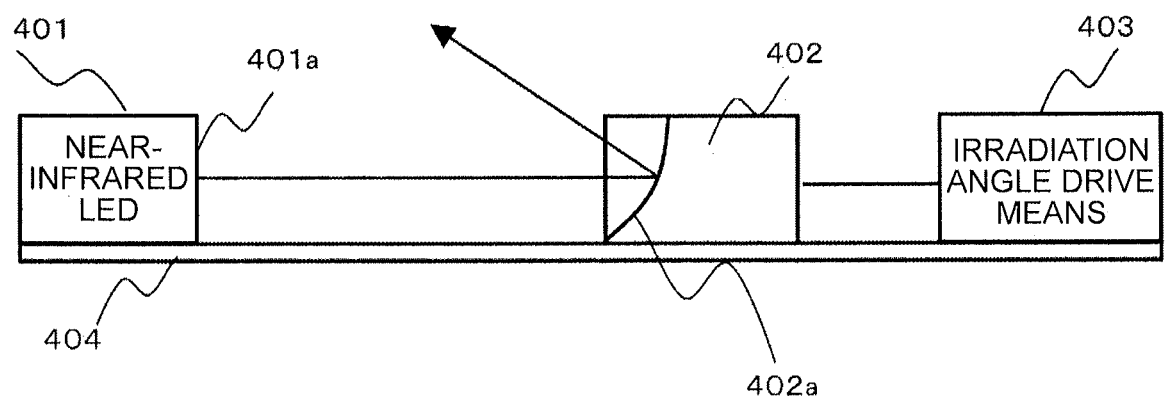
FIG. 4 is a diagram showing a configuration example of the illumination means of the first embodiment.

In order to obtain the foregoing object, the specific configuration of the illumination means 105 is now explained with reference to FIG. 4. In FIG. 4, reference numeral 401 is a near-infrared light source, reference numeral 402 is a reflecting mirror, reference numeral 403 is an irradiation angle drive means for controlling the angle of a reflecting surface 402a of the reflecting mirror 402, and reference numeral 404 is a substrate which supports the respective parts of the illumination means 105.

The near-infrared light source 401 irradiates near-infrared light from a light-emitting surface 401a in parallel with the substrate. The irradiated near-infrared light is reflected by the reflecting surface 402a which forms a curved surface of the reflecting mirror 402, and is irradiated in a direction toward the upper part of the finger. The reflecting surface 402a is adjusted so that the near-infrared light is concentrated near the top side of the finger. The reflecting surface 402a is controlled so that the irradiation angle is changed by the irradiation angle drive means 403, and the proper irradiation angle can be obtained even when the size of the finger changes. Specifically, considered may be a method of taking photos of a plurality of images while changing the irradiation angle within a certain angular range, and selecting the image that is suitable for finger vein authentication among the photographed images.

Figure 5:
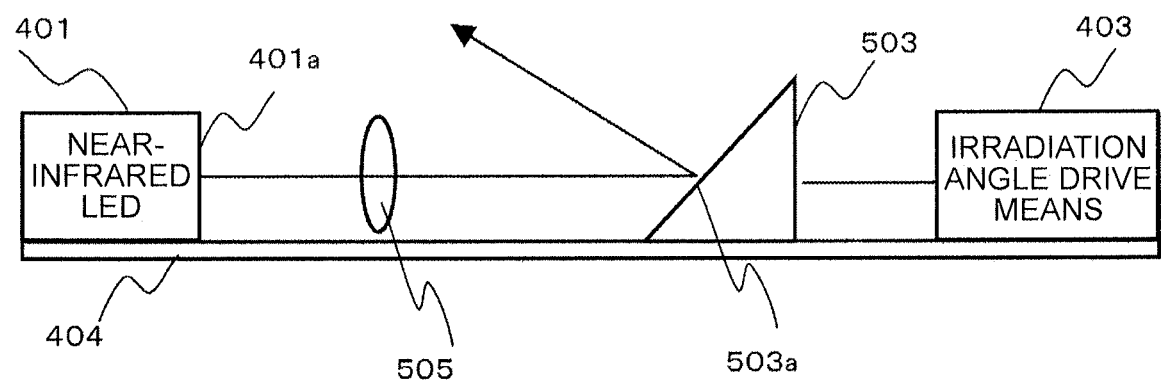
FIG. 5 is a diagram showing a configuration example of another illumination means of the first embodiment.

The configuration of another illumination means 105 in this embodiment is shown in FIG. 5. In FIG. 5, reference numeral 503 is a reflecting mirror, reference numeral 505 is a condensing lens, and the same parts as FIG. 4 are given the same reference numeral. In the example of FIG. 4, while the reflecting surface of the reflecting mirror was a curved surface, the reflecting mirror 503 of FIG. 5 is a planar mirror, and the condensing lens 505 condenses near-infrared light near the top side of the finger. According to this embodiment, because it is possible to acquire a vein image under the proper illumination condition by changing the irradiation angle (irradiation condition) of near-infrared illumination to match the size and shape of the finger that changes for each person or finger, it is possible to achieve the effect of improving the authentication accuracy. Moreover, according to this embodiment, because it is possible to realize a thin near-infrared illumination, the finger vein authentication module can be installed in a small and thin digital device such as a smartphone.

Embodiment 2

In the first embodiment, while a processing method based on a single CMOS was explained, the authentication accuracy can be improved if it is possible to acquire a vein pattern of a broader part more clearly.

In order to achieve the above, considered may be a combination of a wide-angle imaging means capable of taking on a broad photographing range, a micro lens array as an optical system of the same size, and a flat sensor having a broad area, but if the sensor area is increased, there are problems in that the component costs may increase or problems in terms of manufacture, such as that a sensor of the necessary resolution cannot be acquired.

In order to resolve the foregoing problems, a plurality of CMOS sensors may be disposed in an array to broaden the photographed area. By combining sensors having a relatively small photographed area, an inexpensive system can be configured.

Figure 6:
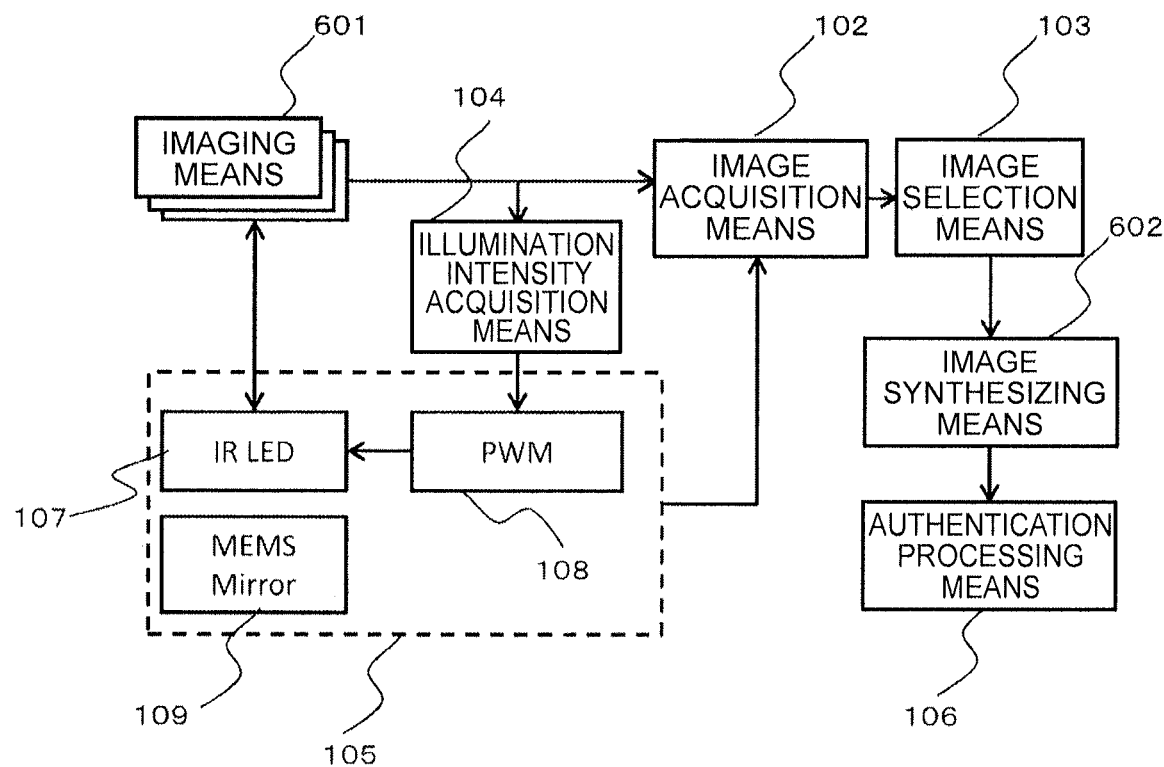
FIG. 6 is a block diagram showing the processing circuit of the finger vein authentication device of the second embodiment.
Figure 7:
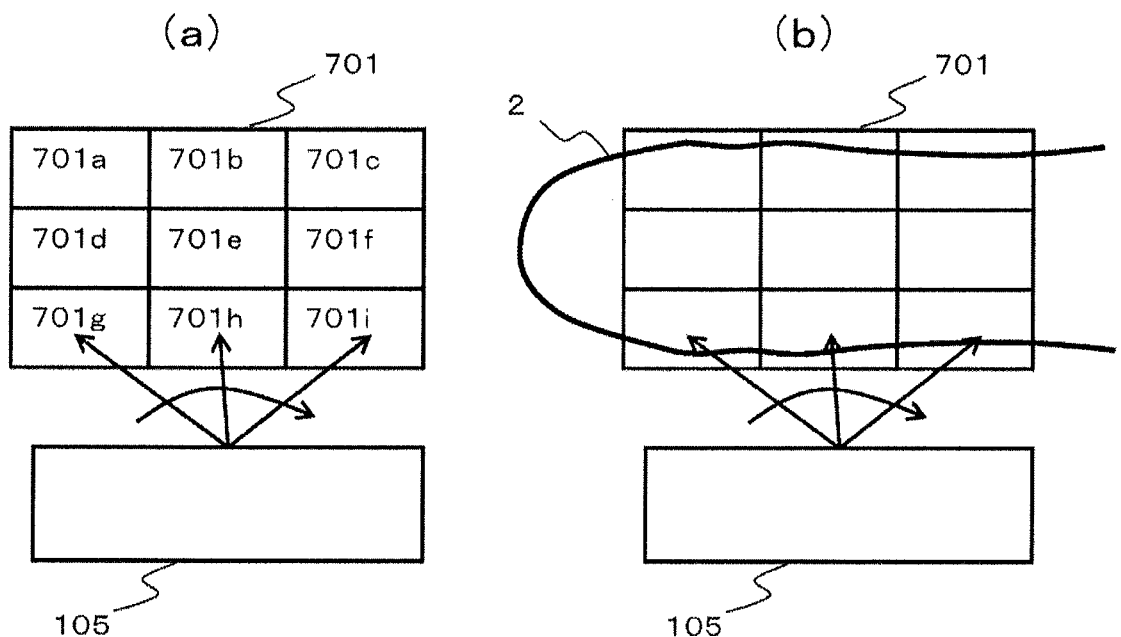
FIG. 7 is a schematic diagram of the second embodiment.

FIG. 6 and FIG. 7 are diagrams for explaining the second embodiment. FIG. 6 is a block diagram of the second embodiment. FIG. 7 is a schematic diagram of the second embodiment, and shows an example of using 9 CMOS sensors. The same processing blocks as the first embodiment are given the same reference numeral. Reference numeral 601 is a plurality of CMOS sensors, and reference numeral 602 is an image synthesizing means.

In FIG. 7(*a*) and FIG. 7(*b*), reference numeral 2 is a finger to be photographed, reference numeral 701 shows the photographing range of a plurality of CMOS sensors, and reference numeral 701*a* to 702*i* respectively show the photographing range of the CMOS sensors.

The images photographed by the plurality of CMOS sensors 601 are temporarily stored in the image acquisition means 102, and partial images photographed under the condition of proper irradiation angle by the image selection means 103 are read, and sent to the image synthesizing means 602. The image synthesizing means 602 synthesizes the input partial images, and creates an overall image. At this stage, the image synthesizing means 602 performs image processing such as brightness correction and distortion correction to the partial images of the respective CMOS sensors. The image synthesizing means retains in advance data for performing the foregoing corrections, and performs image processing based on the foregoing data.

The illumination means 105 has a variable irradiation angle as with the first embodiment, and is able to take photos while changing the irradiation angle and take photos under proper illumination conditions. Because photos of the respective parts are taken at a broad range with a plurality of CMOS sensors, the irradiation angle is changed two-dimensionally, and photos are taken under proper illumination conditions for each CMOS sensor.

In order to select partial images of proper illumination, the image selection means 103 performs image processing to the partial images according to the irradiation angle, and selects partial images of the proper illumination condition. The method of this image processing may be the same as the first embodiment.

In order to perform processing of synthesizing an overall image from the partial images photographed under a different illumination condition, the image synthesizing means 602 needs to perform special processing so that there will be no level difference in brightness at the connecting part. As an example of this processing, performed is processing of setting an area that overlaps at a predetermined amount with the photographing range of each CMOS sensor; that is, setting an area that is photographed by both adjacent CMOS sensors, and taking the arithmetic mean of the images with the foregoing area as the connecting part of the images between the CMOS sensors.

The synthesized image is input to the authentication processing means 106, and the authentication processing is executed based on the vein pattern.

According to this embodiment described above, because the authentication processing can be executed based on the vein image of the part of the finger of the broad range, it is possible to yield the effect of improving the authentication accuracy by using inexpensive parts.

Embodiment 3

The third embodiment shows an example of a finger vein authentication device based on the control method of taking a photo of the vein image of a broad range with one CMOS sensor and selecting proper illumination for each part of the image. As the illumination of the finger vein authentication, it is possible to irradiate illumination of the same brightness from either side of the finger and input a vein image that is balanced left and right. However, considered may be a configuration of placing a light source on either the left side or the right side due to restrictions on installing the device or restrictions on size. In the foregoing case, because the irradiation angle of proper illumination on the left side and the right side of the finger on angle is different, it is possible to improve the authentication accuracy by selecting images photographed based on proper illumination for each part, synthesizing an overall image from the partial images and performing authentication, and acquiring the proper vein image.

Figure 8:
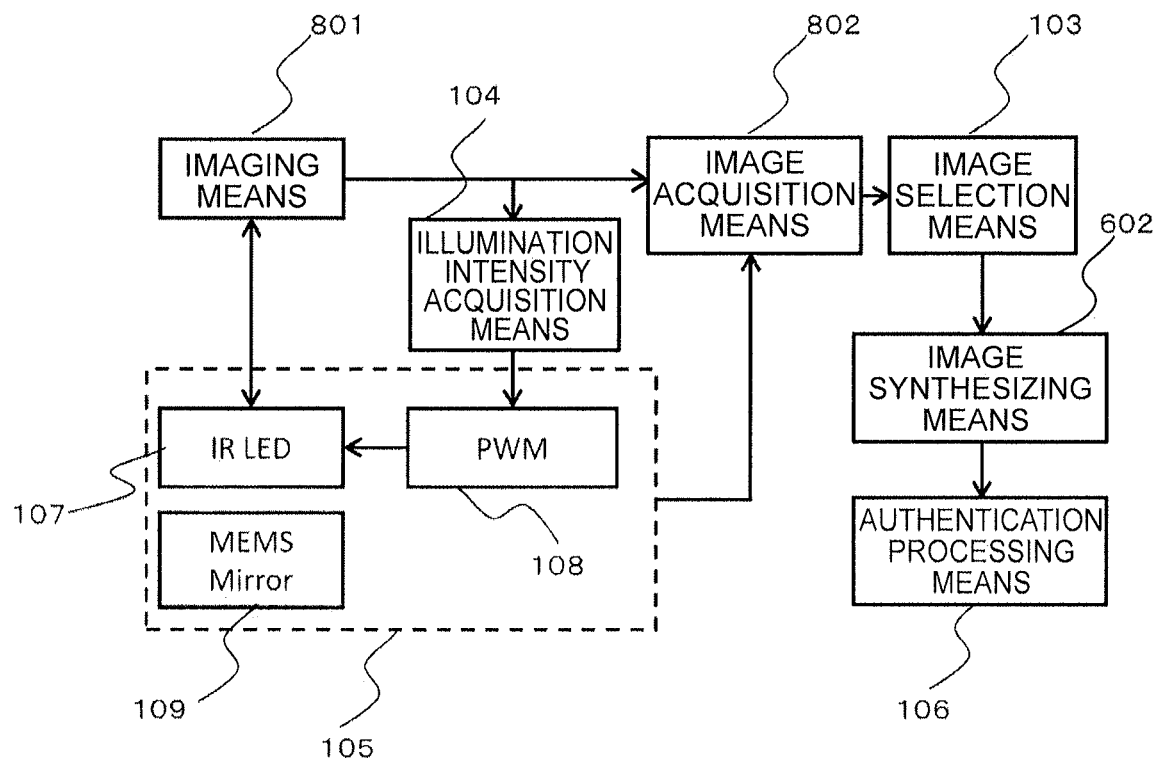
FIG. 8 is a block diagram showing the processing circuit of the finger vein authentication device of the third embodiment.
Figure 9:
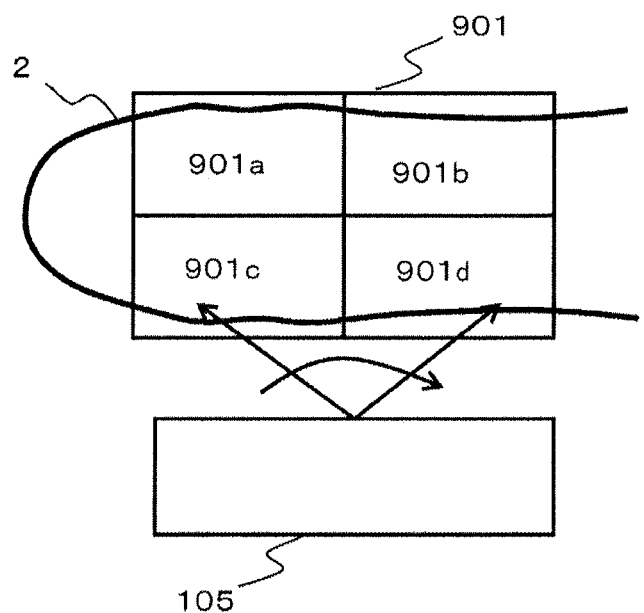
FIG. 9 is a schematic diagram of the third embodiment.

FIG. 8 and FIG. 9 are a processing block diagram and a schematic diagram for explaining the third embodiment. The same processing blocks as the same as the first embodiment or the second embodiment are given the same reference numeral. In FIG. 8, reference numeral 801 is an imaging means, and can be realized with a CMOS sensor or the like. Reference numeral 802 is a partial image acquisition means, and is a block for temporarily retaining the partial images corresponding to the respective irradiation angles of the illumination means 105. Reference numeral 602 is an image synthesizing means, and performs the same function as the image synthesizing means 602 shown in the second embodiment.

FIG. 9 is a schematic diagram explaining a case of dividing the imaging means into 4 parts and performing processing, reference numeral 901 shows the photographing range of the imaging means 801, and 901*a* to 901*d* show the respective divided regions. The illumination means 105 changes the illumination angle to achieve the illumination condition that is suitable for the photograph of the respective parts.

The image selection means 103 reads the partial images of the proper illumination condition from the partial images stored in the partial image acquisition means 802, and sends the read partial images to the image synthesizing means 602. The image synthesizing means 602 synthesizes the partial images and generates one overall image. The authentication processing means 106 executes authentication processing with the overall image generated by the image synthesizing means 602 as the input vein image.

According to this embodiment described above, even in cases where a proper image cannot be obtained from the overall image with one illumination condition (illumination angle), it is possible to synthesize an overall image from partial images in which illumination is optimized for each part, improve the quality of the image for use in the authentication processing, and thereby improve the authentication accuracy.

Embodiment 4

A smartphone is normally configured by being equipped with a main CMOS sensor for taking standard photos and videos. Here, the main CMOS sensor is equipped with an infrared removal filter and configured to remove unwanted signal components.

When installing a finger vein authentication module in a smartphone, in addition to the main CMOS sensor, a CMOS sensor for finger vein authentication is added, and a total of two CMOS sensors may be installed. Here, an infrared transmission filter is mounted on the finger vein authentication CMOS sensor, and a near-infrared photo is taken. In this embodiment, a control method for finger vein authentication using a main CMOS sensor is explained.

Figure 10:
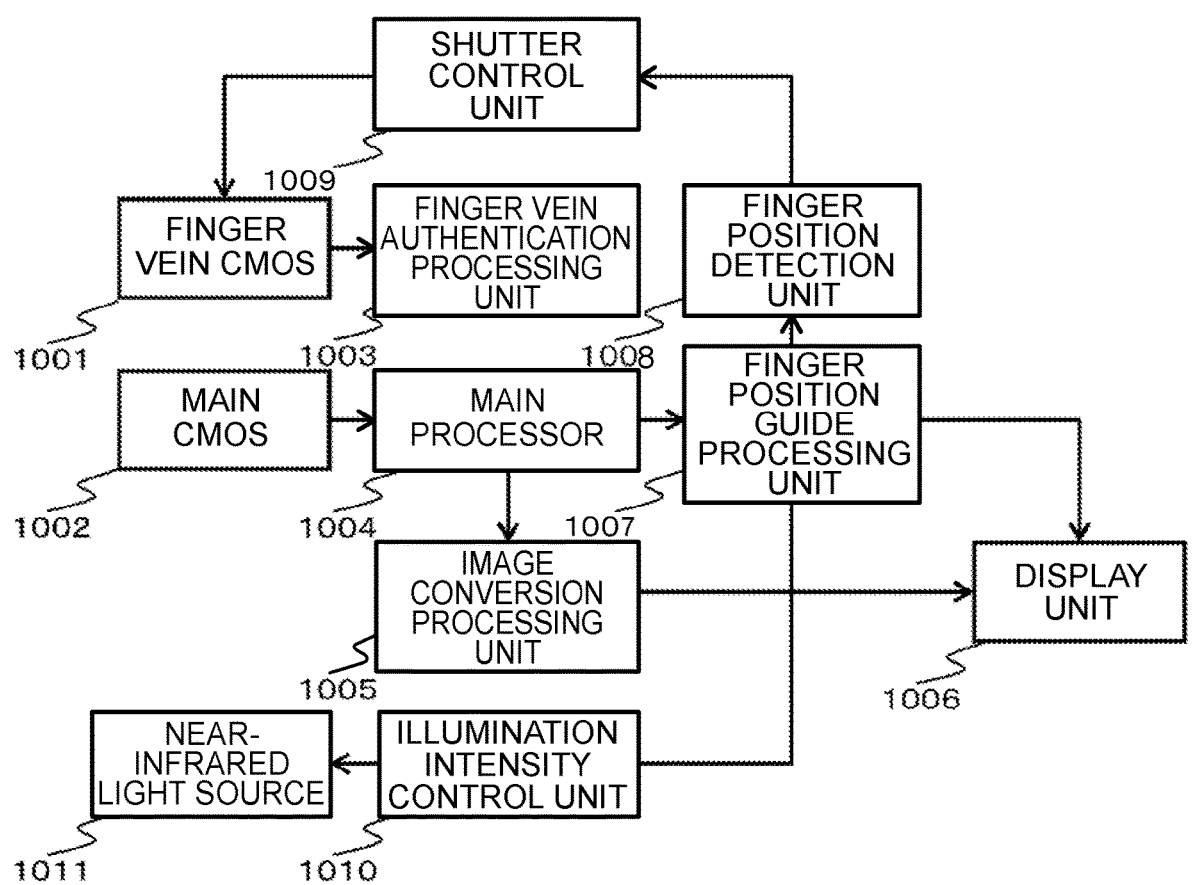
FIG. 10 is a block diagram showing the processing circuit of the finger vein authentication device of the fourth embodiment.
Figure 11:
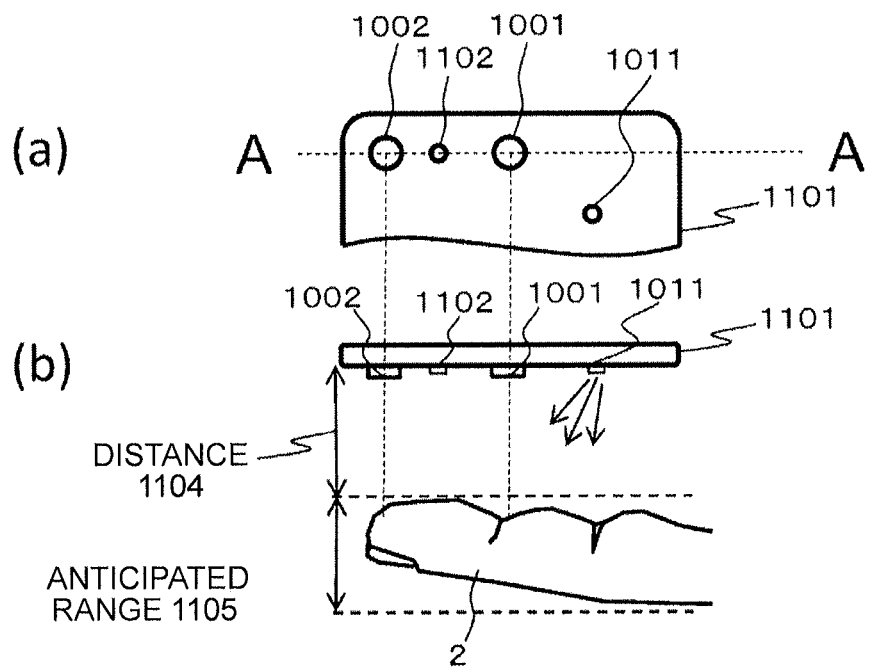
FIG. 11 is a schematic diagram of the fourth embodiment.
Figure 12:
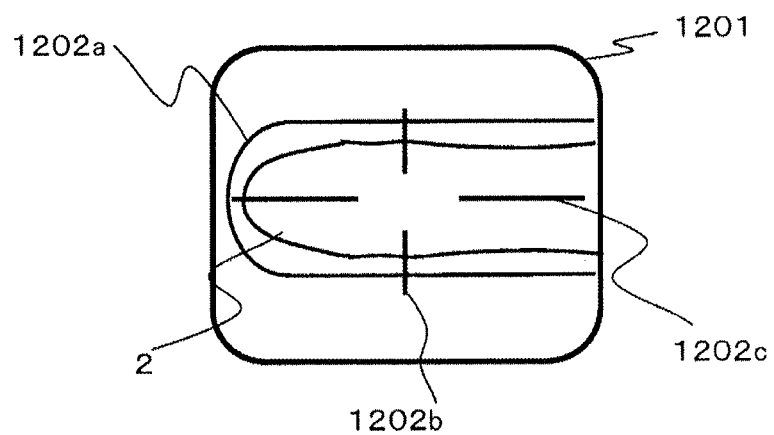
FIG. 12 is a display example of the finger position guide of the fourth embodiment.

FIG. 10, FIG. 11, and FIG. 12 are a processing block diagram, a schematic diagram, and an example of a display method of a finger position guide to be displayed on a smartphone for explaining the fourth embodiment.

In FIG. 10, reference numeral 1001 is a finger vein authentication CMOS sensor, reference numeral 1002 is a main CMOS sensor, reference numeral 1003 is a finger vein authentication processing block, reference numeral 1004 is a main processor unit of a smartphone and a block that also performs the image processing of the main CMOS sensor, reference numeral 1005 is an image conversion processing unit, reference numeral 1006 is a display unit of a smartphone, reference numeral 1007 is a finger position guide processing unit, reference numeral 1008 is a finger position detection unit, reference numeral 1009 is a shutter control unit, reference numeral 1010 is an illumination intensity control unit, and reference numeral 1011 is a near-infrared light source.

FIG. 11 is a schematic diagram showing the appearance of a smartphone equipped with the processing block of FIG. 10, and shows the same reference numeral is assigned to the same parts as FIG. 10. Moreover, FIG. 11 is configured from FIG. 11(a) and FIG. 11(b), and the A-A cross section of FIG. 11(a) is FIG. 11(b). Reference numeral 1101 of FIG. 11 is the body of a smartphone equipped with the finger vein authentication module. Reference numeral 1104 of FIG. 11(b) is the distance of closest approach of the finger 2 for taking a photo of the vein, and reference numeral 1105 is the anticipated photographing range for taking a photo of the vein.

In FIG. 12, reference numeral 1201 is the image display range of the finger position guide displayed on the display unit 1006 captured by the main CMOS sensor 1002, reference numeral 1202 is the display of the finger position guide to be displayed, reference numeral 1202a is the proper size of the anticipated finger, reference numeral 1202b is the center point in the longitudinal direction of the finger, and reference numeral 1202c is the center line of the finger.

Due to differences in the mounting position in comparison to the finger vein authentication CMOS sensor 1001, the image of the main CMOS sensor 1002 is converted into an image corresponding to the image captured from the position of the finger vein authentication CMOS sensor 1001 by converting the angle of view based on image processing. The converted image is displayed as the finger position guide 1201 on a part of the display unit 1006 as shown in FIG. 12, and is used for adjusting the placement of the finger presented by the user; that is, the position and direction of the finger.

When the direction of the center line of the finger that is actually presented is inclined relative to a predetermined direction, the contour line of the finger may be extracted based on image processing, the angle thereof may be calculated, and the amount of inclination may be displayed as a numerical value or a line segment on the display unit 1006.

The main processor unit 1004 generates an image of the finger position guide 1201 with the finger position guide processing unit 1008, and superimposes and displays the generated image on the display unit 1006. The finger position detection unit 1007 calculates the distance between the smartphone and the finger based on the image of the sensor of the main CMOS sensor and the sensor control related to the main CMOS sensor; for example, control signals related to auto focus. Based on the distance information, the shutter control unit 1009 controls the shutter of the finger vein authentication CMOS sensor 1001, and controls the photography of the finger vein image.

The finger position guide processing unit 1008 controls the illumination control unit 1010 based on the distance information of the fingered detected by the finger position detection unit 1007, and controls the irradiation of the near-infrared light from the near-infrared light source 1011. In FIG. 11, the control method of near-infrared light irradiation is explained. When the finger 2 is within a predetermined position range and within an anticipated photographing range 1105 from the distance of closest approach 1104, the illumination control unit controls the illumination intensity of the illumination means 1011 based on the foregoing distance information, and performs proper near-infrared illumination. If the finger is deviated from a predetermined range, the illumination intensity of the illumination means 1011 may be turned OFF to suppress power consumption due to unneeded illumination.

In the same manner described above, when the finger falls within a predetermined position range based on the position information of the finger calculated by the finger position guide processing unit 1008, the shutter control unit 1009 acquires the finger vein image by shutting OFF the shutter of the finger vein authentication CMOS sensor 1001.

Because it is possible to take a photo of the finger vein image at a proper timing by controlling the finger vein authentication CMOS sensor 1001 and the illumination means 1011 based on the image of the main CMOS sensor as described above, and additionally control the near-infrared illumination properly according to the position of the finger, it is possible to reduce the power of near-infrared illumination simultaneously with improving the user-friendliness of the finger vein authentication device.

Moreover, according to this embodiment, of the two CMOS sensors 1001 and 1002, it is possible to conceal the image of the finger vein authentication CMOS sensor 1001 for use in biometric authentication, and this is suitable for security measures. The biometric authentication processing is limited to the blocks of the CMOS sensor 1001 and the finger vein authentication processing unit 1003, and it is possible to realize a configuration where biological information such as the raw image and vein pattern of the finger vein from the main processor unit 1004 that executes the application program of a smartphone.

According to this embodiment, it is possible to realize a control method of a finger vein authentication device that is suitable for a small device such as a smartphone.

REFERENCE SIGNS LIST

1 . . . finger vein authentication device, 2 . . . finger, 101 . . . imaging means, 102 . . . image acquisition means, 103 . . . image selection means, 104 . . . illumination intensity acquisition means, 105 . . . illumination means, 106 . . . authentication processing means, 107 . . . near-infrared light source, 108 . . . PWM signal generation means, 109 . . . MEMS mirror

The invention claimed is:

1. A finger vein authentication device which takes a photograph of a blood vessel pattern of a finger of an individual, and authenticates the individual by matching the photographed blood vessel pattern with a registered blood vessel pattern, comprising:
   a plurality of imaging sensors;
   an illumination device which is disposed on a substantially same plane as the plurality of imaging sensors, the illumination device comprising a light source and a movable reflecting mirror in which an angle of reflection is variable, the illumination device irradiates a finger to be captured by the plurality of imaging sensors by directing light from the light source to the movable reflecting mirror in a direction parallel to the plane and reflecting light from the movable reflecting mirror at a variable angle;
   a processor in communication with the plurality of imaging sensors, the processor comprising:
      an image selection circuit which selects an image according to the angle of reflection of the light; and
      an authentication processing circuit which performs authentication processing using the image selected by the image selection circuit.

2. The finger vein authentication device according to claim 1,
   wherein the illumination device is disposed at a position shifted from a position where the finger is placed to a position where the finger vein authentication device is projected, and irradiates a back part of the placed finger with light.

3. The biometric authentication device according to claim 1,
   wherein the image selection circuit performs correction processing related to brightness or distortion of a partial image for each imaging sensor.

4. The finger vein authentication device according to claim 1, further comprising:
   a guide imaging sensor; and
   a display which superimposes and displays, on an image captured by the guide imaging sensor, a guide for adjusting placement of a subject's finger to a proper position and direction.

5. The finger vein authentication device according to claim 1,
   wherein the the direction of light from the light source is fixed.

6. A finger vein authentication device according to claim 1,
   wherein light irradiated by the illumination device is infrared light, and
   wherein the plurality of imaging sensors are capable of detecting infrared light.

7. A finger vein authentication device which takes a photograph of a blood vessel pattern of a finger of an individual, and authenticates the individual by matching the photographed blood vessel pattern with a registered blood vessel pattern, comprising:
   a plurality of imaging sensors and an optical lens assembly which capture images of different parts of the finger;
   an illumination device which is disposed on a substantially same plane as the plurality of imaging sensors, and irradiates a finger to be captured by the plurality of imaging sensors with light in which an irradiation angle is variable;
   a processor in communication with the plurality of imaging sensors, the processor comprising:
      an image selection circuit which selects an image according to an irradiation angle from a plurality of partial images output by the plurality of imaging sensors; and
      an authentication processing circuit which performs authentication processing using the image selected by the image selection circuit;
      an image synthesizing circuit which synthesizes an overall image from the partial images output by the image selection circuit; and
      a correction processing circuit which corrects brightness or distortion of each partial image,
   wherein the image selection circuit selects a partial image of illumination according to the finger for each of the plurality of imaging sensors,
   wherein the image synthesizing circuit synthesizes an overall image from the selected partial images, and
   wherein the authentication processing circuit performs the authentication processing using the overall image.

* * * * *